US012763203B2

(12) United States Patent
Baronov et al.

(10) Patent No.: US 12,763,203 B2
(45) **Date of Patent: *Oct. 13, 2026**

(54) SYSTEMS AND METHODS FOR OPTIMIZING MEDICAL CARE THROUGH DATA MONITORING AND FEEDBACK TREATMENT

(71) Applicant: Etiometry Inc., Boston, MA (US)

(72) Inventors: Dimitar V. Baronov, Weston, MA (US); Evan J. Butler, New Haven, CT (US); Jesse M. Lock, Winchester, MA (US)

(73) Assignee: Etiometry Inc., Dedham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/296,080

(22) Filed: Aug. 11, 2025

(65) Prior Publication Data

US 2026/0038680 A1 Feb. 5, 2026

Related U.S. Application Data

(63) Continuation of application No. 18/083,949, filed on Dec. 19, 2022, now Pat. No. 12,387,842, which is a
(Continued)

(51) Int. Cl.
*G16H 40/63* (2018.01)
*A61B 5/0205* (2006.01)
(Continued)

(52) U.S. Cl.
CPC .......... *G16H 40/63* (2018.01); *A61B 5/0205* (2013.01); *A61M 5/1723* (2013.01);
(Continued)

(58) Field of Classification Search
CPC .............. A61M 5/1723; A61M 27/002; A61M 16/0003; G06F 19/3456; G06F 19/34;
(Continued)

(56) References Cited

U.S. PATENT DOCUMENTS

2013/0190581 A1 * 7/2013 Al-Ali .................. A61B 5/0295
600/324
2019/0298270 A1 * 10/2019 Al-Ali .................... A61B 5/684

OTHER PUBLICATIONS

Connor et al., Hypoplastic left heart syndrome, Orphanet Journal of Rare Diseases, 2007, 2:23, 5 pages (Year: 2007).*
(Continued)

*Primary Examiner* — Jason S Tiedeman
(74) *Attorney, Agent, or Firm* — Nutter, McClennen & Fish, LLP

(57) ABSTRACT

Systems, methods, and computer-readable media for providing a decision support solution to medical professionals to optimize medical care through data monitoring and feedback treatment are provided herein. In another embodiment, a computer-implemented method for modeling patient outcomes resulting from treatment in a specific medical area includes receiving patient-specific data associated with a patient, determining a plurality of possible patient states under which the patient can be categorized, a current patient state under which the patient can be categorized and determining probabilities of the patient transitioning from any of the possible patient states to every other possible patient state.

9 Claims, 7 Drawing Sheets

Related U.S. Application Data continuation of application No. 15/881,255, filed on Jan. 26, 2018, now Pat. No. 11,557,394, which is a continuation of application No. 14/535,149, filed on Nov. 6, 2014, now abandoned, which is a continuation of application No. 13/689,029, filed on Nov. 29, 2012, now abandoned, which is a continuation of application No. 13/698,319, filed as application No. PCT/US2012/027713 on Mar. 5, 2012, now abandoned.

(60) Provisional application No. 61/449,176, filed on Mar. 4, 2011.

(51) Int. Cl.

| | |
|---|---|
| ***A61M 5/172*** | (2006.01) |
| ***A61M 16/00*** | (2006.01) |
| ***A61M 27/00*** | (2006.01) |
| ***G16H 20/10*** | (2018.01) |
| ***G16H 50/20*** | (2018.01) |
| ***G16H 50/50*** | (2018.01) |
| *A61B 5/02* | (2006.01) |
| *A61B 5/145* | (2006.01) |
| *A61B 5/1455* | (2006.01) |

(52) U.S. Cl.

CPC ...... *A61M 16/0003* (2014.02); *A61M 27/002* (2013.01); *G16H 20/10* (2018.01); *G16H 50/20* (2018.01); *G16H 50/50* (2018.01); *A61B 5/02* (2013.01); *A61B 5/14532* (2013.01); *A61B 5/14542* (2013.01); *A61B 5/14546* (2013.01); *A61B 5/1455* (2013.01)

(58) Field of Classification Search

CPC ........ G16H 50/20; G16H 50/50; G06Q 50/22; A61B 5/14546; A61B 5/14542; A61B 5/14532; A61B 5/0402; A61B 5/02

USPC .......................................................... 705/2, 3

See application file for complete search history.

(56) References Cited

OTHER PUBLICATIONS

Lopes et al., A computer-based matrix for rapid calculation of pulmonary hemodynamic parameters in congenital heart disease, Annals of Thoracic Medicine—vol. 4, Issue 3, Jul.-Sep. 2009, 4 pages (Year: 2009).*

Caplan et al., Diffusion of Innovative Approaches to Managing Hypoplastic Left Heart Syndrome, Arch Pediatr Adolesc Med. 1996; 150:487-490, 4 pages (Year: 1996).*

Barnea et al., Coronary autoregulation and optimal myocardial oxygen utilization, Basic Res Cardio187:290-301 (1992), 12 pages (Year: 1992).*

Hinton et al., Hypoplastic Left Heart Syndrome is Heritable, Journal of the American College of Cardiology, vol. 50, No. 16, 2007, 6 pages (Year: 2007).*

Tabbutt et al., Impact of Inspired Gas Mixtures on Preoperative Infants With Hypoplastic Left Heart Syndrome During Controlled Ventilation, Circulation, available at http://www.circulationaha.org, 6 pages (Year: 2001).*

Barnea et al., Oxygen Delivery in Newborns With Congenital Heart Disease, IEEE 0-7803-2050-6/94, 2 pages (Year: 1994).*

Jobes et al., Carbon Dioxide Prevents Pulmonary Overcirculation in Hypoplastic Left Heart Syndrome, The Society of Thoracic Surgeons, 0003-4975/92, 2 pages (Year: 1992).*

* cited by examiner

Time at state = 0 min

Time at state = 30 min

Time at state = 60 min

Time at state = 90 min

Fig. 5B
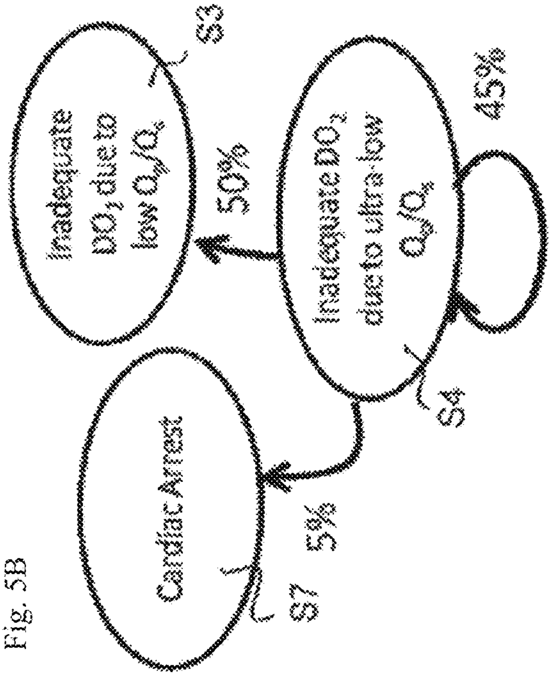
Treatment with INO @ 20 ppm
Fig. 5A
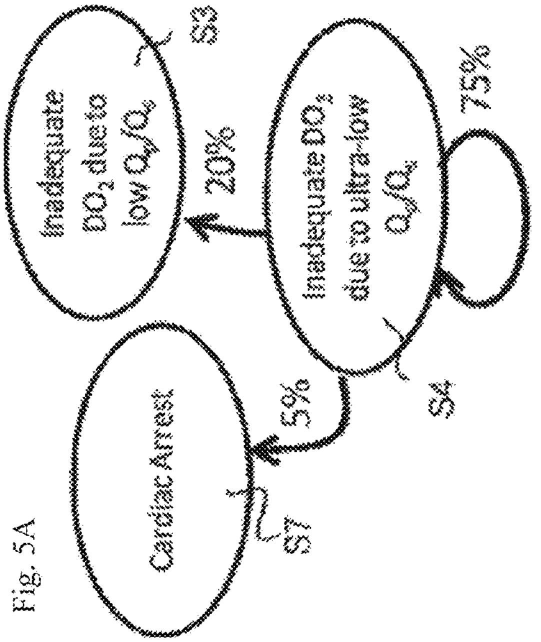
No treatment
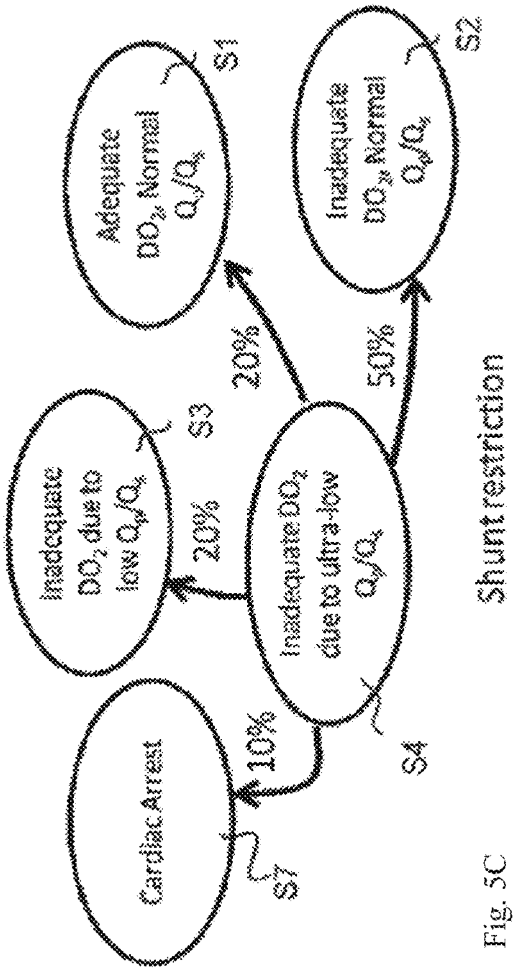
Shunt restriction
Fig. 5C

SYSTEMS AND METHODS FOR OPTIMIZING MEDICAL CARE THROUGH DATA MONITORING AND FEEDBACK TREATMENT

CROSS REFERENCE TO RELATED APPLICATIONS

The present application is a continuation of U.S. patent application Ser. No. 18/083,949, filed Dec. 19, 2022 [practitioner's file 3816-11803], which is a continuation of U.S. patent application Ser. No. 15/881,255, filed Jan. 26, 2018 [practitioner's file 3816-11801], which is a continuation of U.S. patent application Ser. No. 14/535,149, filed Nov. 6, 2014, which is a continuation of U.S. patent application Ser. No. 13/689,029, filed Nov. 29, 2012, which is a continuation of U.S. patent application Ser. No. 13/698,319, filed Nov. 16, 2012, which is the National Stage Entry of PCT/US12/27713, filed Mar. 5, 2012, which claims priority from U.S. Provisional patent Application No. 61/449,176 filed Mar. 4, 2011, the disclosures of which are incorporated by reference herein in their entireties.

GOVERNMENT LICENSE RIGHTS

This invention was made with government support under contract number W81XWH-11-C-0086 awarded by the Department of Defense. The government has certain rights in the invention.

BACKGROUND

Practicing medicine is becoming increasingly more complicated due to the introduction of new sensors and treatments. As a result, clinicians are confronted with an avalanche of information, which needs to be evaluated and well understood in order to prescribe the optimal treatment from the multitude of available options, while reducing patient risks. One environment where this avalanche of information has become increasingly problematic is the Intensive Care Unit (ICU). There, the experience of the attending physician and the physician's ability to assimilate the available physiologic information have a strong impact on the clinical outcome. It has been determined that hospitals which do not maintain trained intensivists around the clock experience a 14.4% mortality rate as opposed to a 6.0% rate for fully staffed centers. It is estimated that raising the level of care to that of average trained physicians across all ICUs can save 160,000 lives and $4.3 Bn annually. As of 2012, there is a shortage of intensivists, and projections estimate the shortage will only worsen, reaching a level of 35% by 2020.

Therefore, there is a clear need for decision support systems in the ICU which can raise the level of care in facilities which lack trained intensivists.

BRIEF SUMMARY

Technologies are provided herein for providing a decision support solution to medical professionals to optimize medical care through data monitoring and feedback treatment. In one aspect the invention is directed to a system for modeling patient outcomes resulting from treatment in a specific medical area, includes a processor coupled to a memory having computer-executable instructions stored thereon, which when executed by the processor, cause the processor to receive patient-specific data associated with a patient. The system can determine possible patient states for the patient based on the data received, determine a current patient state under which the patient can be categorized, and determine probabilities of the patient transitioning from any of the possible patient states to every other possible patient state.

In another aspect, the invention is directed to a computer-implemented method for modeling patient outcomes resulting from treatment in a specific medical area includes receiving patient-specific data associated with a patient, determining a plurality of possible patient states under which the patient can be categorized, a current patient state under which the patient can be categorized and determining probabilities of the patient transitioning from any of the possible patient states to every other possible patient state.

In yet another aspect, the invention is directed to a computer-readable medium having computer-executable instructions stored thereon, which when executed by a computer, cause the computer to receive patient-specific data associated with a patient, determine possible patient states under which the patient may be categorized and a current patient state under which the patient can be categorized, and determine probabilities of the patient transitioning from any of the possible patient states to every other possible patient state.

BRIEF DESCRIPTION OF THE DRAWINGS

It should be understood at the outset that although illustrative implementations of one or more embodiments of the present disclosure are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

FIG. 5A, FIG. 5B, and FIG. 5C illustrate a subset of the exemplary condition network of FIG. 3 after exposing a patient to various treatment plans in accordance with various embodiments of the present disclosure;

DETAILED DESCRIPTION

Figure 1:
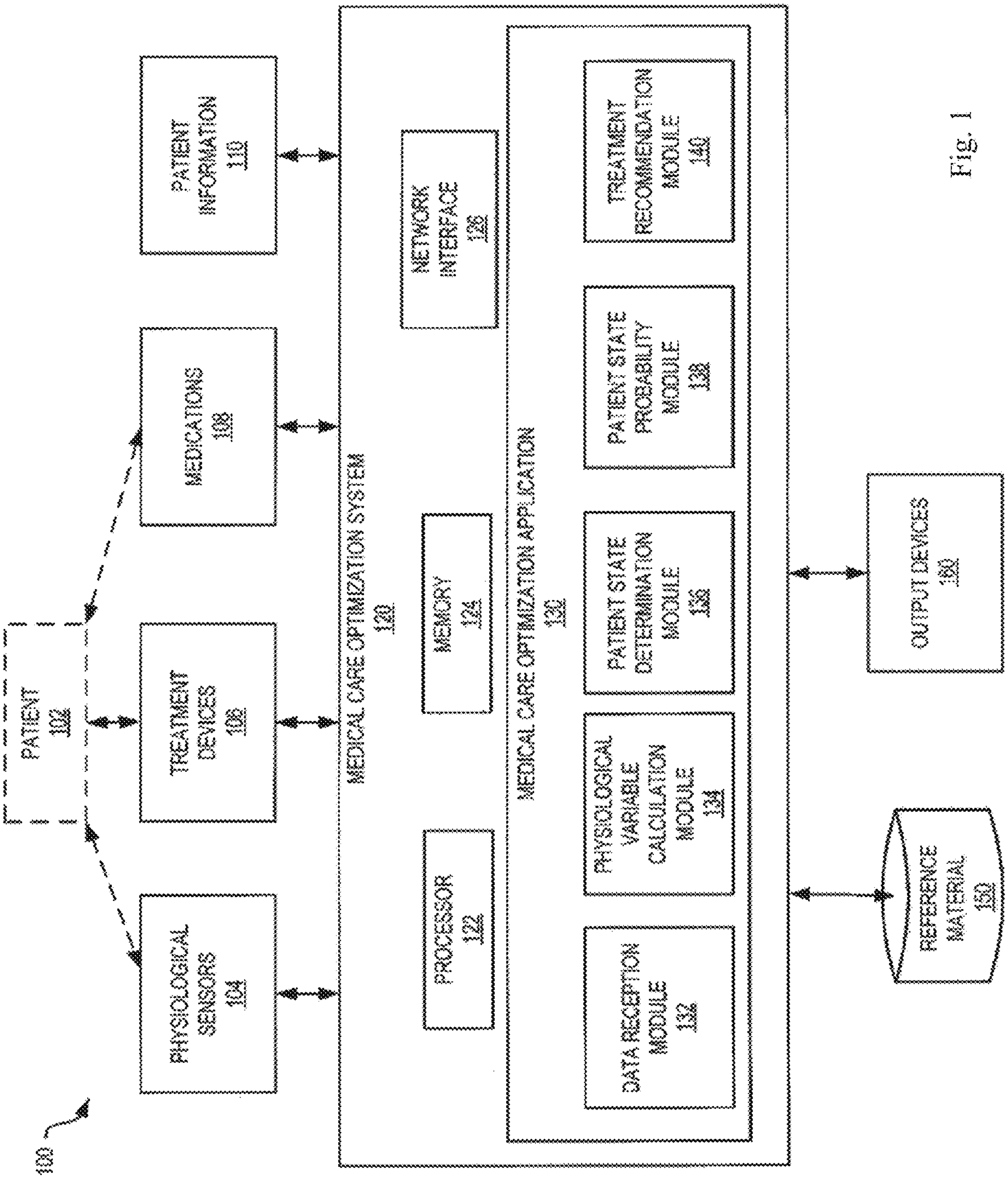
FIG. 1 illustrates a medical care optimization environment for providing health providers assistance in clinical decision making in accordance with various embodiments of the present disclosure.

Technologies are provided herein for providing a decision support solution to medical professionals to optimize medical care through data monitoring and feedback treatment. The technologies described herein can be embodied as a method of optimizing medical care or as decision support tool configured to operate with real-time monitoring systems that are capable of collecting patient information available from a wide range of sources, such as bedside monitors, lab work, medical records, prescribed treatments, amongst others. This information, along with historical data of similar types of patients, can be used to achieve a paradigm shift from a signal-driven monitoring system to an event-driven monitoring system. That is, instead of the physician being confronted with various physiologic signals and test results, the physician is presented with a qualitative description of the patient's clinical state, the possible clinical states to which the patient may transition, and the probabilities associated with the patient transitioning to each of the possible clinical states from each of the other possible clinical states. The occurrence of a patient transitioning from one possible clinical state to another may be referred to as an event and in an event-driven monitoring system, the physician is focusing on the patient's clinical state as a whole and the possible clinical states to which the patient can transition, instead of focusing on individual signals associated with the multitude of physiological measurements. In this way, the physician may be able to better gauge the risks associated with the patient and formulate a treatment plan based on such risks.

The technologies described herein provide for mathematical models of patient physiology to be merged with expert knowledge of the qualitative behavior of patients in different conditions and under different treatments. The resulting solution allows for the prediction of probable evolutions of the patient's clinical course given the available treatments, and for this information to be presented to physicians in an easily understandable clinical language with which they are comfortable. This also assures that all available information is accounted for by the physicians, independent of their level of training, thereby raising the level of care.

Besides presenting the acquired physiologic information and the consequences of the available treatments in an intuitive way, the technologies described herein enable additional benefits for optimizing medical care. First, the ability to calculate the probabilities for various possible evolutions of the clinical course enables context dependent alerts. In this case, an alert can be triggered when the probability for a specific adverse event is higher than a pre-specified acceptable threshold. Additionally, acuity metrics can be derived based on the calculated likelihood a patient's condition deteriorates.

Second, the technologies described herein enable the utility of these treatments to be quantified by calculating probable future clinical courses under the various available treatments. As a result, the technologies described herein can estimate the optimal treatment and either recommend it to the clinician or render the optimal treatment automatically via the use of infusion pumps, ventilators or any other peripheral medical devices.

The present disclosure will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

$S_i$ is a particular patient state that is recognizable by a clinician from collected physiological data. Examples of particular patient states include hypotension with sinus tachycardia, hypoxia with myocardial depression, amongst others.

A particular patient population can exhibit a finite number of possible patient states, $\Sigma=\{S_1, S_2, S_3, \ldots, S_n\}$, in which patients from the patient population can be categorized during their clinical course. Therefore, the clinical course of an individual patient can be described as a sequence of states, $S_A \rightarrow S_B \rightarrow S_C \rightarrow S_D$, where $S_A$, $S_B$, $S_C$, and $S_D$ may represent any one of the possible patient states $S_1$, $S_2$, $S_3$, . . . . $S_N$. A patient from the particular patient population can only be categorized in only one patient state at any given time. Given that a patient is in a state $S_i$ the marginal probability that the patient transitions to a new state $S_j$ in a particular time horizon is given by $p_{ij}$.

The treatment applied to a patient can be described by an input vector $U=\{b_1, b_2, \ldots, b_k, d_1, d_2, \ldots, d_l\}$, which contains effect site medication concentrations $B=\{b_1, b_2, \ldots b_k\}$ (as a non-limiting example, for cardiac medications, the effect site may be the myocardium), and inputs from bedside medical devices $D=\{d_1, d_2, \ldots, d_l\}$ (as a non-limiting example, ventilators, extracorporeal membrane oxygenation machine, heaters, dialysis machine, and others).

It is assumed that the patient physiology is completely described by a vector of physiologic variables, $\Phi=\{\varphi_1, \varphi_2, \ldots, \varphi_m\}$, which can be directly measured or estimated from a combination of different physiologic sensors. For example, the physiologic variable Cardiac Output can be estimated by the Fick's equation by sensing mixed venous oxygenation, arterial oxygenation, and oxygen consumption.

Referring now to the figures, FIG. 1 illustrates a medical care optimization environment 100 for providing health providers, such as physicians, nurses, or other medical care providers, assistance in making clinical decisions about a patient 102 in accordance with various embodiments of the present disclosure. A patient 102 may be coupled to one or more physiological sensors 104 that may monitor various physiological parameters of the patient. These physiological sensors 104 may include but are not limited to, a blood oximeter, a blood pressure measurement device, a pulse measurement device, a glucose measuring device, one or more analyte measuring devices, an electrocardiogram recording device, amongst others. In addition, the patient may be coupled to one or more treatment devices 106 that are configured to administer treatments to the patient 102. In various embodiments, the treatments 106 may be administered in one or more ways, including but not limited to oral, intravenous, and topical medications, therapy, exposure, amongst others. In addition, the patient 102 may further be treated with medications 108, which may also be administered to the patient in one or more ways, including but not limited to orally, intravenously, or topically. By way of the present disclosure, the patient 102 may be afforded improved medical care over existing methods. A medical care optimization system 120, generally referred to herein as the system 120, may be configured to receive patient related information, including real-time information related to the patient's physiology, treatments being provided to the patient, medications being administered to the patient, and other patient related information 110, which may include the patient's medical history, previous treatment plans, results from previous and present lab work, allergy information, predispositions to various conditions, and any other information that may be deemed relevant to make informed decisions regarding the patient's condition and risks, or any combination thereof. For the sake of simplicity, the various types of information listed above will generally be referred to hereinafter as "patient-specific information". In addition, the system 120 may be configured to utilize the received information, determine possible patient states, determine a patient state from the possible patient states in which the patient is currently categorized, determine the probabilities of transitioning into each of the possible patient states, as well as determine various treatment options and the risks associated with such treatment options, which can then be presented to a medical care provider, including but not limited to a physician, nurse, or other type of clinician.

The system 120, in various embodiments, includes one or more of the following: a processor 122, a memory 124 coupled to the processor 122, and a network interface 126 configured to enable the system 120 to communicate with other devices over a network. In addition, the system 120 may include a medical care optimization application 130 that may include computer-executable instructions, which when executed by the processor 122, cause the system 120 to be able to afford improved medical care to patients, such as the patient 102.

The medical care optimization application 130 includes, for example, a data reception module 132, a physiological variable estimation module 134, a patient state determination module 136, a patient state probability module 138, and a treatment recommendation module 140 or any combination of the above. In an exemplary embodiment, the data reception module 132 may be configured to receive physiological data from the physiological sensors 104, treatment administration information from the treatment devices 106, medication administering information, and other patient related information, including information collected from the medical devices 104, treatment information from treatments 106, and any other information that may be deemed relevant to make informed decisions regarding the patient's condition and risks, and any combination thereof of the preceding elements. Treatment information may be defined as any information that is related to any treatment that is or has been rendered to a patient.

The physiological variable estimation module 134 may, for example, be configured to utilize the information received by the data reception module 132 and estimate various physiological variables based on the information received. For instance, the variable oxygen delivery cannot be measured through a physiological sensor, but is determined by measuring cardiac output. Possible methods of measuring cardiac output, include but are not limited to, direct measurement through thermodilution, or indirect estimation by substituting mixed venous oxygen content, arterial oxygen content, and oxygen consumption in the Fick equation. It should be appreciated that physiological variables also include physiological variable that can be directly measured by one or more physiologic sensors.

The patient state determination module 136 may, for example, be configured to determine the possible patient states under which the patient may be categorized. Examples of particular patient states include hypotension with sinus tachycardia, hypoxia with myocardial depression, compensated circulatory shock, cardiac arrest, hemorhage, amongst others. In addition, these patient states may be specific to a particular medical condition, and the bounds of each of the patient states may be defined by threshold values of various physiological variables and data. In various embodiments, patient state determination module 136 may determine all possible patient states using one or more of the following: information gathered from reference materials, information provided by health care providers, physiological data of the patient, other patient-specific information, amongst others. The references materials may be stored in a database 150 or other storage device that is accessible to the medical care optimization application 130. These reference materials may include material synthesized from reference books, medical literature, surveys of experts, physician provided information, and any other material that may be used as a reference for providing medical care to patients. In some embodiments, the patient state determination module 136 may first identify a patient population that is similar to the patient. By doing so, the patient state determination module 136 may be able to use relevant historical data based on the identified patient population to determine the possible patient states.

The patient state determination module 136 is capable of also determining the patient state under which the patient is currently categorized, referred to herein as the current patient state. The current patient state of the patient can be determined by analyzing, amongst other things, recent patient-specific information from the patient, including but not limited to real-time physiological data. In some embodiments, the patient state determination module 136 can determine all possible patient states for a patient population and can determine the current patient state of the patient. Additional details related to the patient state determination module 136 will be provided below during a discussion of FIGS. 3-7.

Once the patient state determination module 136 determines the possible patient states under which the patient can be categorized, the patient state probability module 138 is able to determine probabilities associated with the patient transitioning from any patient state to any other patient state or remaining in any particular patient state. The patient state probability module 138 may do so by analyzing the patient-specific information, analyzing historical evidence generated from other patients' patient-specific information, and other information available from the reference material 150. In addition, the patient state probability module 138 may also utilize information received from physicians, medical professionals, scientists, and the like to provide hypothetical risk assessments on patients with particular patient profiles. This information can then be generalized and applied algorithmically to determine the probabilities associated with the patient transitioning from one patient state to any other patient state or remaining in a particular patient state. Additional details related to the patient state probability module 138 will also be provided below during a discussion of FIGS. 3-7.

In various embodiments, if the patient's physiology is changing, either due to treatment being received, or due to the natural changes in the patient's physiology over time, the patient state probability module 138 may be configured to determine updated probabilities of a patient transitioning from one patient state to any other patient state based on the changes in the patient's physiology, or based on other information being provided that may influence the probabilities associated with transitions between the patient states. In some embodiments, the patient state probability module 138 may be configured to determine hypothetical updated probabilities of a patient transitioning from one patient state to any other patient state based on hypothetical assumptions. For example, to determine hypothetical probabilities of a patient transitioning from one patient state to another patient state based on providing a hypothetical treatment, the patient state probability module 138 may utilize historical data to hypothesize how the patient's physiology will change over time based on rendering a particular treatment option to the patient. The patient state probability module 138 may then determine probabilities associated with rendering the hypothetical treatment using the hypothesized changes in patient physiology.

Based on the probabilities determined for each possible transition between patient states, the treatment recommendation module 140 may be configured to provide treatment recommendations. Treatment recommendations are treatment options that may be provided to a patient to improve, for example, the patient's health, quality of life, optimize the cost of care, and other resources, or any combination thereof. In various embodiments, the treatment recommendations may be provided to a health care provider via one or more output devices 160. These output devices include but are not limited to, display units, audio output devices, a printer, or any combination thereof. The treatment recommendation module 140 may also utilize information stored in the reference material 150, and alone or in combination with the patient-specific information, and the probabilities determined for each possible transition between patient states, determine one or more treatment options. Upon determining the treatment options, the treatment recommendation module 140 may be configured to determine which of the treatments appears to be the optimal treatment for the patient at that specific time.

In various embodiments, the treatment recommendation module 140 may be configured to assign a risk index which indicates how likely the patient is to transition from the current patient state to one or more patient states designated as specific morbidity states or a mortality state. Based on this risk index, recommended treatment options may vary. Other types of risks that are considered for determining the recommended treatment include, but are not limited to, morbidity risks, mortality risks, the risks of transitioning into an adverse patient state, the risks associated with transitioning into an improved patient state, and the risks of significantly altering one or more of the physiological variables, risks associated with prolonged hospital stay, or any other risks associated with increased treatment costs to the patient, and the like.

Upon determining the treatment options, the treatment options are then ranked based on the risks described above. The treatment recommendation module 140 may then present, via the output devices 160, the recommended treatment option along with other possible treatment options to the health care provider from which the health care provider can make an informed decision regarding the treatment plan. In some embodiments, the treatment recommendation module may also present additional information, including but not limited to possible complications associated with each treatment option, most likely recovery path and risks associated with the treatment plan. In one embodiment, the treatment recommendation module 140 may be configured to execute the recommended treatment option automatically. As such, the recommended treatment option may send commands to the medical devices and infusion pumps to implement the recommended treatment option, thereby closing the loop between medical sensors and medical treatment.

It should be appreciated that the system is a dynamic system that receives updated patient-specific information periodically. The length of time between receiving updated patient-specific information varies based on the source of the information. Some information may be updated in real-time as it is coming in through a device. In some cases, patient data that is obtained through lab work is updated when the lab work report is entered into the system. The data reception module may provide the information to the remaining modules as the data is received by the data reception module, and the remaining modules may utilize the updated data to perform the functionality associated with the respective modules. This includes updating the current patient state and the probabilities associated with the transitions from each patient state to every other possible patient state upon receiving the updated physiological variable data received.

In various embodiments, the medical care optimization application 130 may include one or more modules that may be configured to perform additional functions. For instance, a context alarm module may be configured to alert the medical provider of changes that may lead to one or more events, including changes in a patient state, changes in risk levels, or probabilities exceeding or falling below threshold values, amongst others. In some embodiments, the medical care optimization application 130 may be configured to automatically alter changes to the treatment being provided to the patient by sending control signals to a particular treatment device 106 causing the treatment device 106 to alter the treatment being provided in accordance with the control signal.

Figure 2:
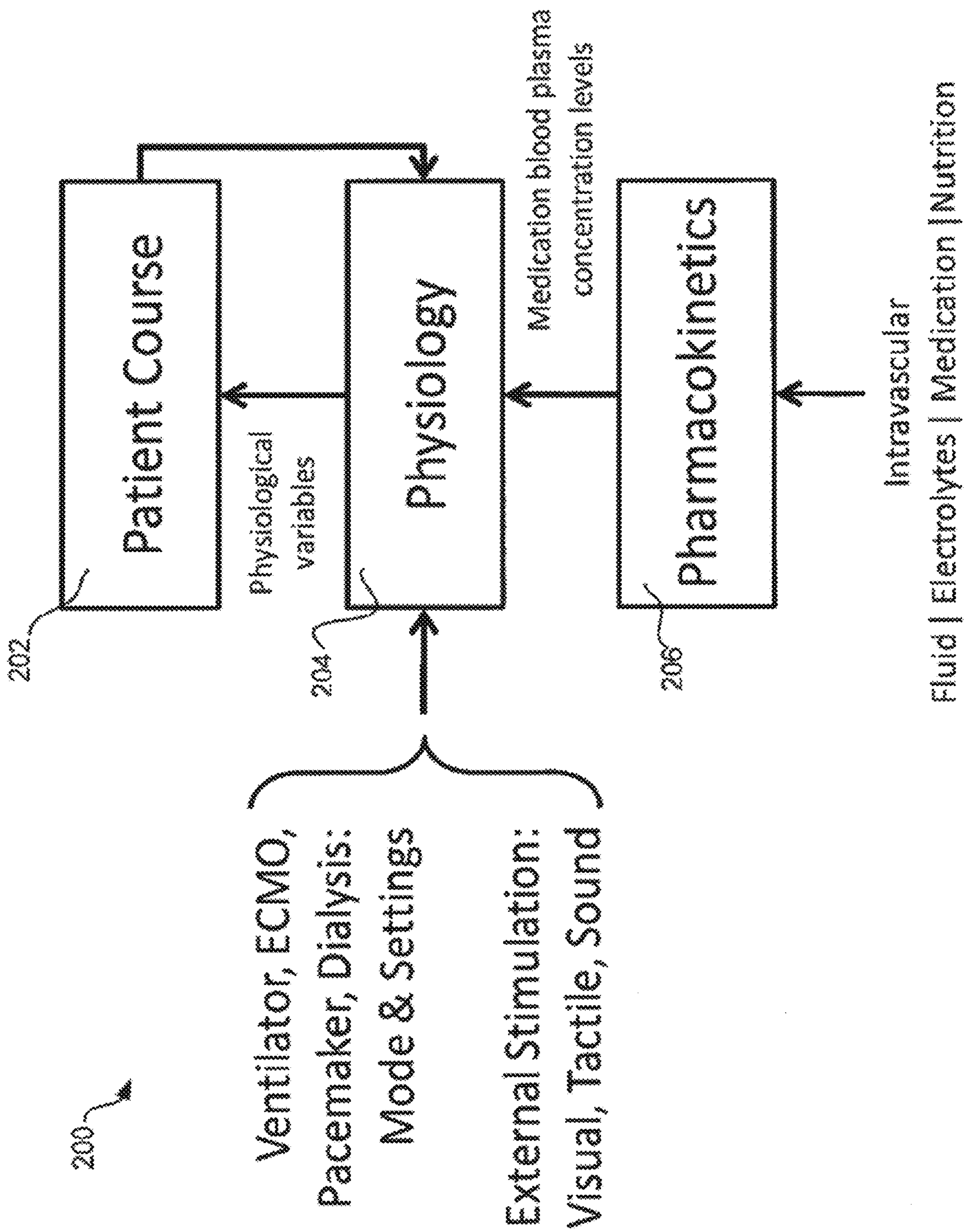
FIG. 2 illustrates a patient model workflow in accordance with various embodiments of the present disclosure.

FIG. 2 illustrates a patient model workflow 200 in accordance with various embodiments of the present disclosure. There are three interacting mathematical models within this architecture. The Patient Course block 202 represents the first component, which is modeled as a connected graph describing all possible patient states for any given patient population. Each of these patient states is represented by a node. Connections between nodes represent potential transitions between patient states which occur as the clinical course progresses. The links in the patient states graph are endowed with probabilities indicating the likelihood of each one-step transition. These probabilities, and respectively the patient's clinical course, may be affected by specific medical interventions, which may then be viewed as mechanisms for control. This evokes similarities between the described model and a Markov Decision Process.

The second component is a mathematical model of the patient's underlying physiology 204, referred to hereinafter as physiology model 204. It is assumed that each patient state or groups of patient states can have different mathematical models. The inputs to the physiology model 204 include medication effect site concentrations (i.e. similar to a pharmacodynamic model which abstracts the relationship between the effect site concentration and particular physiologic variables), ventilator settings, which include everything listed in reference to U in the definitions provided above, and other external stimuli. The outputs correspond to the physiologic variables, which in some embodiments, may include arterial blood pressure, systemic or pulmonary resistance, cardiac output, amongst others.

The third component is a pharmacokinetic model 206 which is used to translate medication infusion rates to effect site (e.g. myocardium) concentration levels. It should be appreciated that the pharmacokinetic model 206 may be configured to receive information associated with electrolyte intake, fluid intake, nutritional intake, and medication intake, amongst others.

As shown in FIG. 2, the three mathematical modules connected together form a dynamic system. The dynamic system incorporates a feedback system to account for changes that alter the patient's physiological variables. A patient may exist in a particular patient state based on the current physiological variables of the patient. As the patient undergoes some treatment, for instance, medications being administered to the patient via the pharmacokinetic model 206 alter the patient's physiological variables. Similarly, medical devices coupled to the patient that are also providing treatment of the patient may also alter the treatment being provided to the patient, thereby causing the physiological variables to alter even more. As such, the physiological model 204 experiences changes, which may lead to a transition from the patient's current patient state to another patient state, or may lead to a change in probabilities associated with the possible patient states, which alters the graph of the patient course block 202. Over time, one or more of the patient's physiological variables are continuously changing, thereby altering the probabilities associated with transitioning to other states. This continuous change results in a real-time dynamic system that allows health care providers to render improved medical care to patients.

The following illustrates how the described invention can be applied to the modeling of the clinical course of a specific patient population under intensive care-post-operatively recovering Hypoplastic Left Heart Syndrome patients after stage one palliation.

Hypoplastic Left Hear Syndrome is a congenital heart defect, which is manifested by an underdeveloped left ventricle and left atrium. As a result, patients suffering from this condition do not have separated systemic and pulmonary blood flows, but instead the right ventricle is responsible for pumping blood to both the body and the lungs. Therefore, the hemodynamic optimization during intensive care involves managing the fractions of the blood flow that pass through the lungs (pulmonary flow $Q_p$) and the body (systemic flow $Q_s$). The optimal hemodynamic is reached when, adequate tissue oxygen delivery, $DO_2$, is achieved for a pulmonary to systemic blood flow ratio, denoted $Q_p/Q_s$, of 1. Often to reach this optimal state the patient physiology passes through other less beneficial states, and the correct identification of these states and the application of proper treatment strategy for each one of them define the quality of the post-operative care. The collection of all these states constitutes the condition network describing this specific population.

Figure 3:
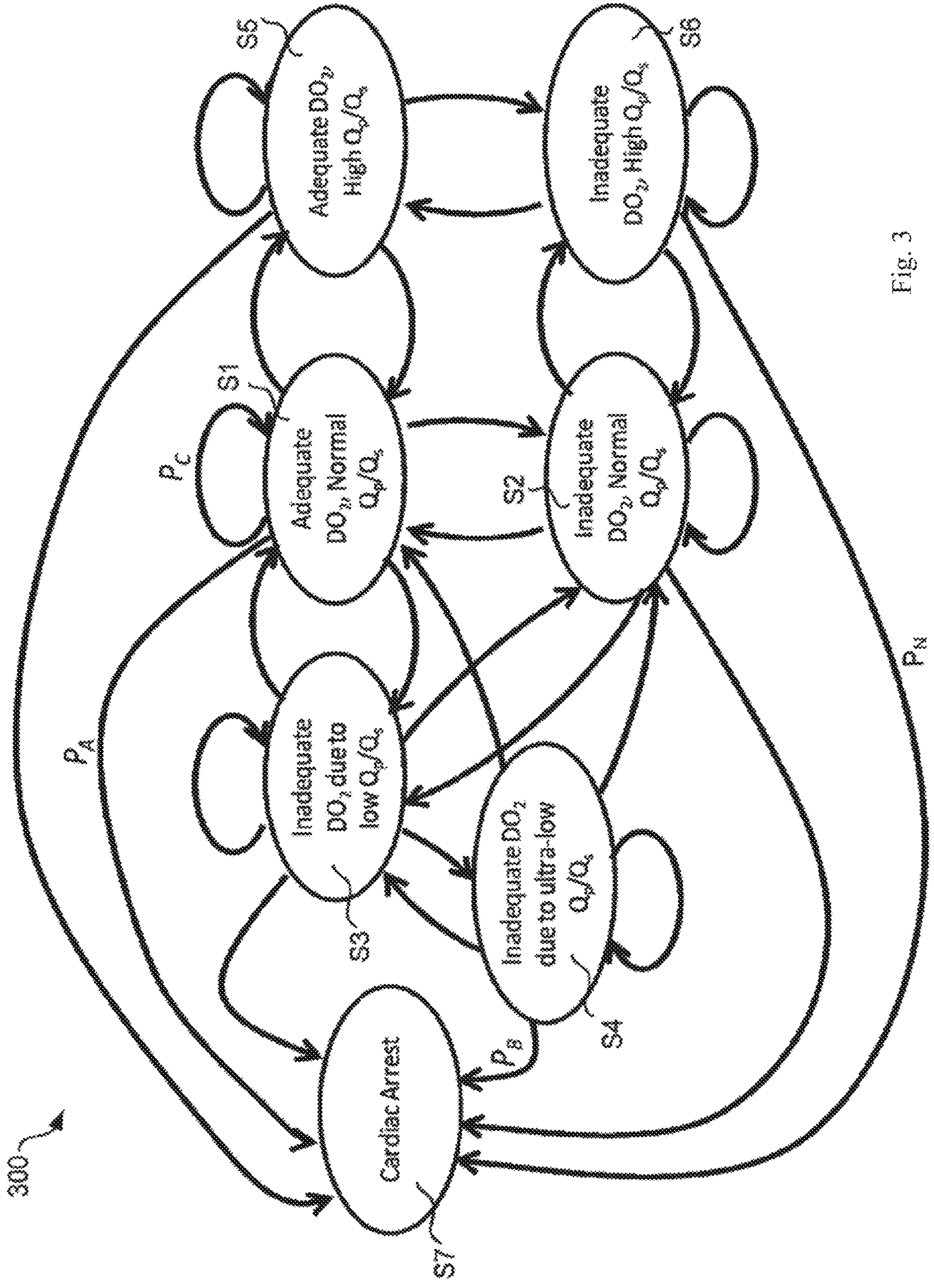
FIG. 3 illustrates an exemplary condition network of possible patient states for patients undergoing intensive care after first stage palliation of hypoplastic left heart syndrome in accordance with various embodiments of the present disclosure.
Figure 4A:
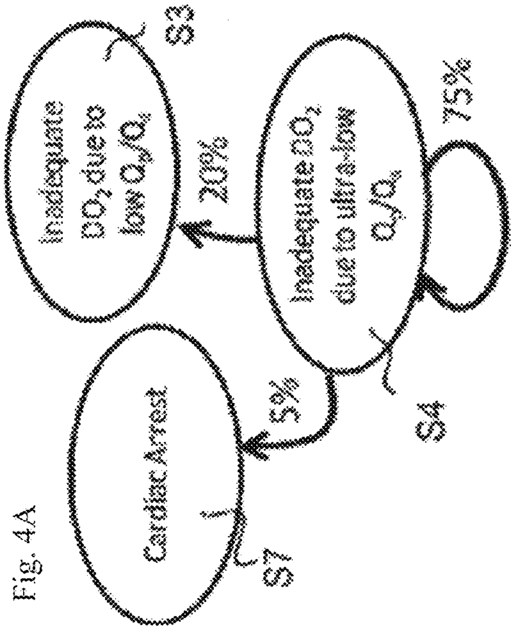
FIG. 4A, FIG. 4B, FIG. 4C, and FIG. 4D illustrate a subset of the exemplary condition network of FIG. 3 at various time intervals without exposing the patient to treatment in accordance with various embodiments of the present disclosure.
Figure 4B:
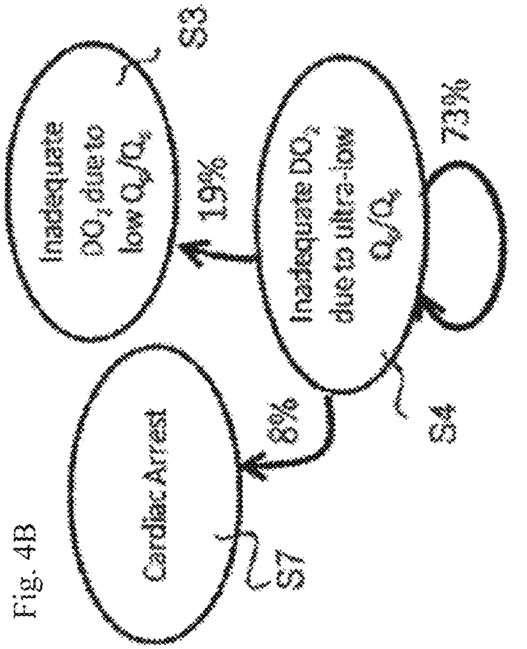
Figure 4C:
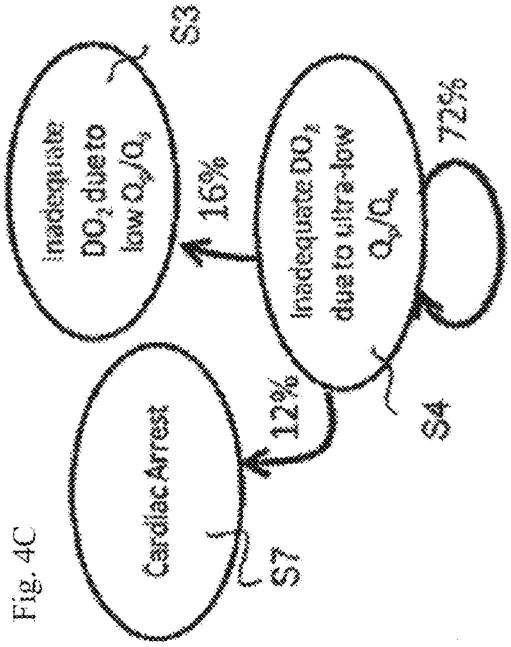
Figure 4D:
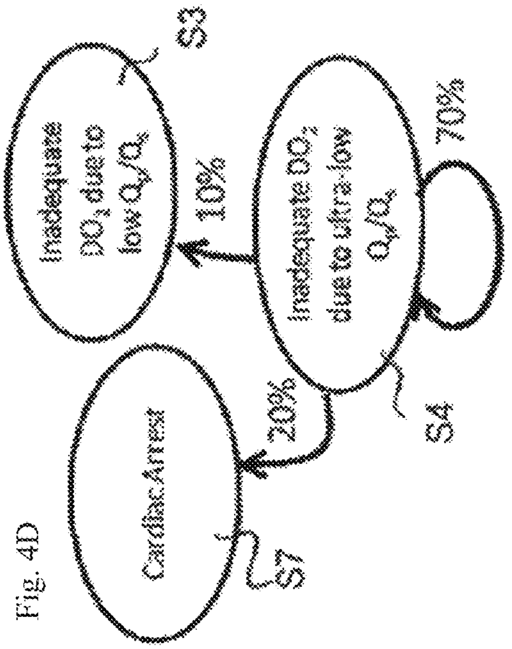

FIG. 3 illustrates an exemplary condition network 300 of possible patient states for patients undergoing intensive care after first stage palliation of hypoplastic left heart syndrome in accordance with various embodiments of the present disclosure. It should be appreciated that although these states may not include all possible states in a real-life setting, the following states have been shown for the sake of simplicity and explanation. Additional information regarding these patient states can be found in Moss and Adams' heart disease in infants, children, and adolescents: including the fetus and young adult, Volume 1 (7th ed., pp. 1005-1038)., Patient state $S_1$ refers to Adequate $DO_2$, Normal $Q_p/Q_s$—This is the optimal state, in which good tissue oxygen perfusion is achieved with minimum work of the heart. A patient in this state is usually weaned from medication and other treatment support.

Patient state $S_2$ refers to Inadequate $DO_2$, Normal $Q_p/Q_s$—In this state, the patient has optimized pulmonary to systemic flow, but not sufficient tissue oxygenation. This is due to inadequate total cardiac output, which is given by $CO=Q_p+Q_s$. A possible treatment in this case is the administration of chronotropic medications, which can raise the heart rate and respectively the total cardiac output.

Patient state S3 refers to Inadequate $DO_2$ due to low $Q_p/Q_s$—In this case, the systemic oxygen delivery is prohibited by the fact that there is not enough blood flow oxygenating through the lungs. This can be corrected by raising the systemic vascular resistance with vasoconstrictor medications, re-directing flow towards the lungs.

Patient state S4 refers to Inadequate $DO_2$ due to ultra-low $Q_p/Q_s$—In this case, even smaller fraction of the blood flow passes through the lungs, e.g. only ⅓ of the total cardiac output is oxygenated. In this extreme case, in addition to increasing systemic vascular resistance, the clinician should consider reducing the pulmonary vascular resistance by administering Nitric Oxide. Alternative, more invasive treatment is to further restrict the shunt through surgical means.

Patient state S5 refers to Adequate $DO_2$, High $Q_p/Q_s$—In this case, although the body is receiving adequate oxygenation, this is achieved in the expense of increased work of the heart. To correct for this, the clinician should lower systemic vascular resistance either through vasodilator medications or through additional sedation.

Patient state S6 refers to Inadequate $DO_2$, High $Q_p/Q_s$—In this case, both the tissue oxygenation is insufficient and the pulmonary to systemic blood flow unbalanced. This should be treated by an increase of cardiac output (e.g. chronotropic medication to increase heart rate) and by decrease of systemic vascular resistance.

Patient state S7 refers to cardiac arrest, which represents a major adverse event from untreated inadequate oxygenation or overworked heart, resulting in a cardiac arrest.

Still referring to FIG. 3, the probabilities $P_A$ and $P_B$ signify, respectively, the probabilities for the patient developing a cardiac arrest in a particular time interval, given adequate oxygen delivery and pulmonary to systemic blood flow ratio close to one, and given compromised hemodynamic with small pulmonary to systemic flow ratio. These probabilities can be calculated by the patient state probability module 138. It should be appreciated that $P_A$ should be much smaller than $P_B$, i.e. given optimized hemodynamic there is a much smaller probability for the patient encountering cardiac arrest. On the other hand, Pc signifies the probability that the patient remains in the same state within the same time interval, i.e. the probability that the patient remains with optimized hemodynamic. Similarly, all arches from the figure can be endowed with probabilities ranging from 0 to 1 or 0% to 100%.

When the system 120 is initialized and no treatment has begun to be administered, the probabilities may be derived from static information, such as medical records, literature, physician inputs, and the like. However, as patient-specific information, such as physiological information and treatment information are provided, the probabilities may be updated based on the patient-specific information being fed to the system 120. The probabilities may be dynamically updated by estimating how the patient is influenced by additional parameters, such as time, as described below with respect to FIG. 4A, FIG. 4B, FIG. 4C and FIG. 4D, and treatments, as described below with respect to FIG. 5A, FIG. 5B, and FIG. 5C. As described above, the patient state probability determination module 138 may be configured to estimate the probabilities and update the probabilities as changes to the patient's physiology are observed.

FIG. 4A, FIG. 4B, FIG. 4C and FIG. 4D illustrate a subset of the exemplary condition network 300 of FIG. 3 at various time intervals without exposing the patient to treatment in accordance with various embodiments of the present disclosure. The simplest influence is the time the patient spends at a particular state, such as patient state S4. After the patient transitions to the patient state S4 with inadequate $DO_2$ due to ultra-low pulmonary to systemic flow ratio, the chances that the patient transitions to a cardiac arrest state increases with time. This is due to the gradual exhaustion of the patient metabolic reserves, consequent acidosis and hypoxia, which increase the chances for cardiac arrest.

FIG. 5A, FIG. 5B, and FIG. 5C illustrate a subset of the exemplary condition network 300 of FIG. 3 after exposing a patient to various treatment plans in accordance with various embodiments of the present disclosure. As described above, another way that the transition probabilities can be influenced is through administering treatment. When a patient is in patient state S3, representing an inadequate $DO_2$ State due to ultra-low pulmonary to systemic flow ratio, there are several treatment options. If nothing is done, the patient will remain in the same state with high probability as indicated in FIG. 5A. If the patient is administered Nitric Oxide, as represented by FIG. 5B, the pulmonary vascular resistance will decrease and therefore there is high probability of transition to a state closer to optimal hemodynamic properties.

Another treatment option is to surgically alter the apex of the shunt, which is represented by FIG. 5C. Although this procedure may have a higher probability for cardiac arrest, there is a zero probability that the patient remains in the same state after it, and high probabilities that the patient transitions to more beneficial hemodynamic states.

Figure 6:
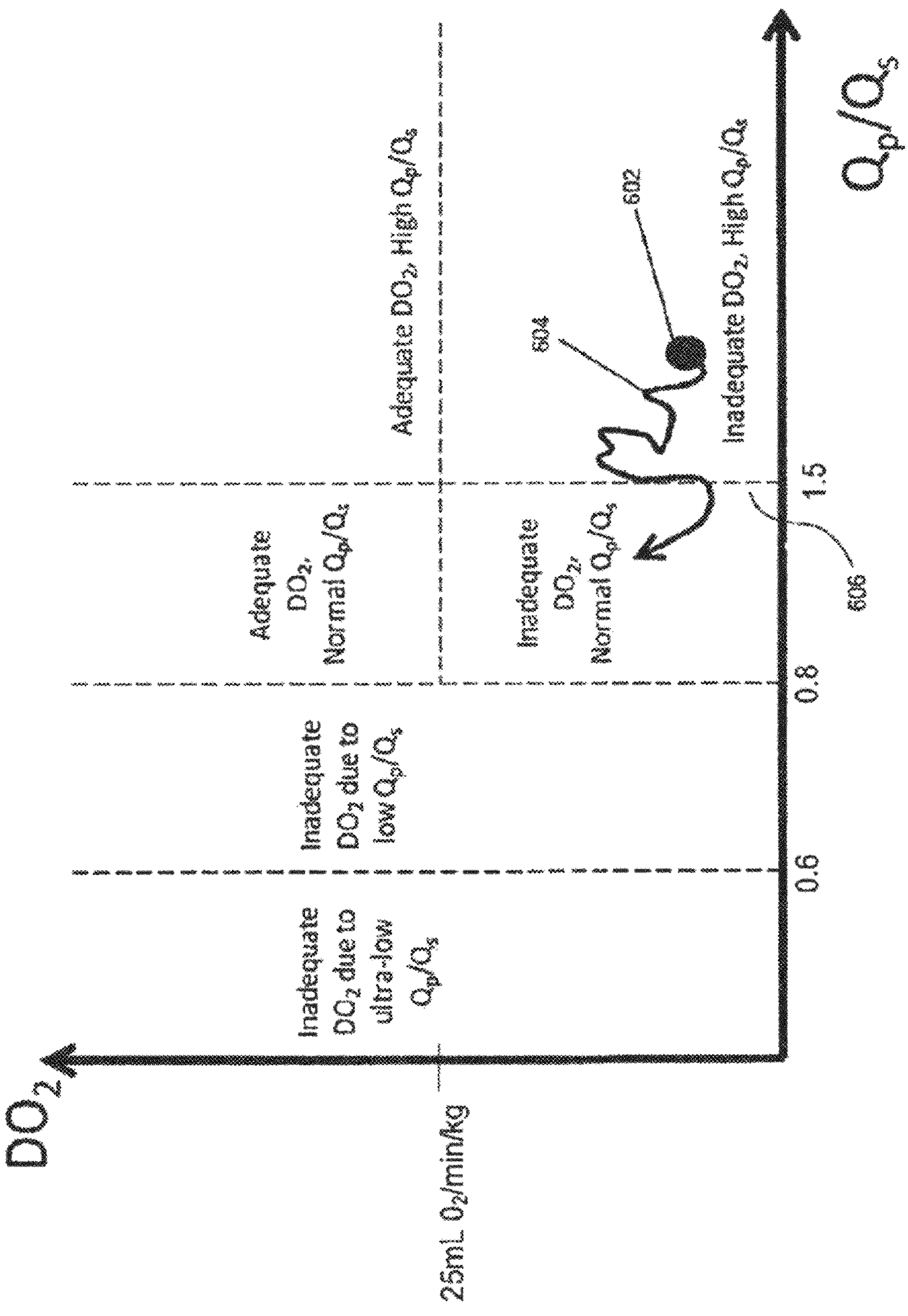
FIG. 6 is a graph illustrating a sample trajectory of the physiologic variables that can cause a transition from one patient state to another in accordance with various embodiments of the present disclosure.

Referring now to FIG. 6, a graph 600 illustrating a sample trajectory of the physiologic variables that can cause a transition from one patient state to another in accordance with various embodiments of the present disclosure is shown. In some embodiments, the probabilities can be further refined and made into functions of measurable physiologic parameters in the following way: first assume that the guiding variables $DO_2$ and $Q_p/Q_s$ form a state space that can be partitioned in the same way as shown in FIG. 6. Assume that for each possible state of the patient there is a set of dynamic equations of the type:

$$\dot{x} = f_{S_1}(x, u, \mu)$$

$$\begin{bmatrix} DO_2 \\ Q_p / Q_s \end{bmatrix} = h(x)$$

where f and h are known functions, x is a set of internal state variables describing the patient physiology, u is the set of treatment inputs, and μ is a random variable underscoring the stochastic nature of the dynamics.

Then, assuming that x can be measured at some time t=0, shown as the initial condition 602 in FIG. 5), possible trajectories x(t) 604 can be simulated for different realizations of the random variable u and the probabilities for various transitions can be calculated. The transitions can be shown in FIG. 6 as the trajectory crosses the boundaries of the partition of the state space 606.

Consider the following example dynamic equation for the patient being in patient state S6 represented by an Inadequate $DO_2$, High $Q_p/Q_s$ State, and receiving a treatment of chronotropic medication and vasodilators:

$$\frac{d}{dt}\begin{bmatrix} x_1 \\ x_2 \end{bmatrix} = \begin{bmatrix} a(x_1 - CO_d(u_1)) \\ b\left(x_2 - \frac{SVR_d(u_2)}{PVR}\right) \end{bmatrix} + \mu(t)$$

$$\begin{bmatrix} DO_2(t) \\ Q_p / Q_s(t) \end{bmatrix} = \begin{bmatrix} \frac{1}{1 + x_2(t)} x_1(t) CpvO_2 - \frac{1}{x_2(t)} CvO_2 \\ x_2(t) \end{bmatrix}$$

where:

$x_1$ cardiac output defined as $x_1 = Q_p + Q_s$ $x_2$ is the pulmonary to systemic blood flow ratio, $Q_p/Q_s$ a is known constant b is known constant $CO_d$ is desired cardiac output which is function of the target site concentration of chronotropes $u_1$.

PVR is pulmonary vascular resistance $SVR_d$ is desired systemic vascular resistance which is function of the target site concentration of vasodilatation drugs, $u_2$.

μ(t) is vector Gaussian white noise with known parameters.

$C_{pv}O_2$ is pulmonary venous oxygen content which is assumed to be known and constant.

$C_vO_2$ is the oxygen consumption which is also known, u1 is the target site concentration of chronotropes $u_2$ is the target site concentration of vasodilation medications The equation set forth above has been reported to be used to derive $DO_2$ as function of $x_1$, $x_2$, $C_{pv}O_2$ and $C_vO_2$ is cited by Barnea, O., Santamore, W. P., Rossi, A., Salloum, E., Chien, S., & Austin, E. H. (1998), "Estimation of oxygen delivery in newborns with a univentricular circulation". Circulation, 98(14), 1407-1413.

Using this equation, the treatment recommendation module 140 of the medical care optimization system 120 can automatically calculate the probabilities of various patient state transitions, given various medication concentrations $(u_1, u_2)$ and given the patient current cardiac output and pulmonary to systemic flow ratio $(x_1(0), x_2(0))$.

The following illustrates another example of how the described invention can be applied to the optimization of pre-hospital care of hemorrhaging trauma victims. In the pre-hospital care of this patient population, there are two major treatment choices differentiating the outcome:

The first treatment choice is the choice of a center where the patient should be driven. In this choice, there is a trade-off between the distance to the center and the center capabilities. Ideally all patients with significant injuries will be delivered to a Trauma I level center, which has optimal capabilities. However, especially in a rural set-up, delivering the patient alive to such a center may not be possible, and therefore the patient may have to be triaged to a non-trauma center. The second treatment choice is the infusion of resuscitative fluid. It has been increasingly appreciated by the medical community that the choice of whether fluid infusion should be initiated and the choice of infusion rate should depend on the transportation time. If the patient is close to a hospital no infusion therapy is recommended. As such, by way of the present disclosure, a health care provider debating these treatment choices can make a more informed decision, which results in optimizing the level of health care being provided to patients.

Figure 7:
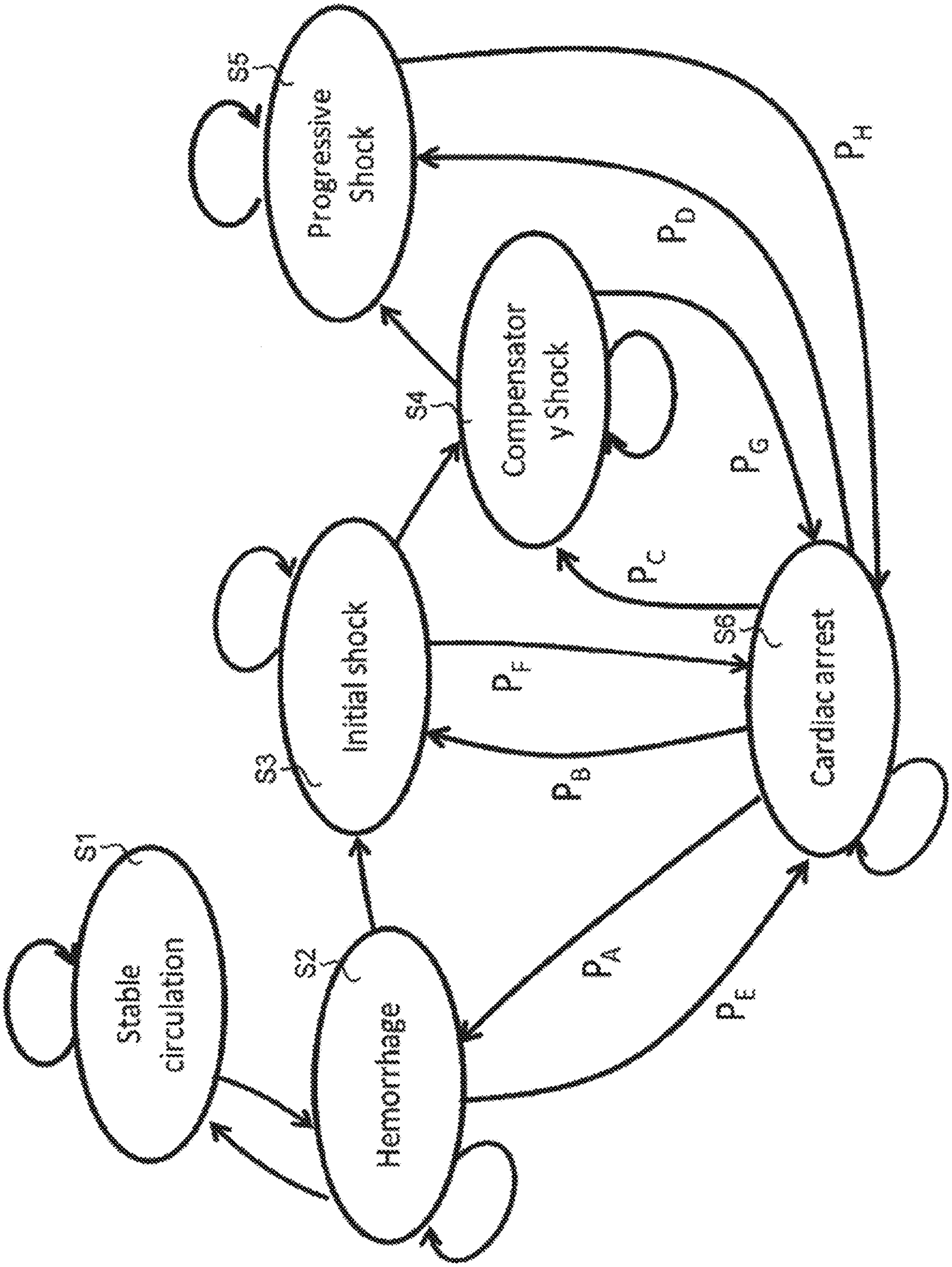
FIG. 7 illustrates an exemplary condition network of possible patient states for patients associated with hemorrhaging trauma in accordance with various embodiments of the present disclosure.

FIG. 7 illustrates an exemplary condition network 700 of possible patient states for patients associated with hemorrhaging trauma in accordance with various embodiments of the present disclosure. It should be appreciated that although these states may not include all possible states in a real-life setting, the following states have been shown for the sake of simplicity and explanation. The major variable guiding the objective identification of the states illustrated in FIG. 7 is the cumulative oxygen deficit (COD). It is defined as the integrated difference between the nominal oxygen consumption ($NvO_2$), and the oxygen consumption ($vO_2$) that can be accommodated by the increasingly depleting oxygen caring capacity of the blood:

$$COD = \int_0^T \frac{\max[0, NvO_2 - vO_2]}{W} dt$$

where W is the weight of the patient.

Still referring to FIG. 7 the following states are illustrated in the condition network 700:

Patient state S1 refers to stable circulation. In this case, homeostasis has been achieved and the remaining blood can assure nominal oxygen consumption.

Patient state S2 refers to hemorrhaging with uncompromised oxygen consumption. In this state, although the patient is losing blood, the patient fluids still have enough oxygen carrying capacity to assure normal oxygen balance.

Patient state S3 refers to initial shock. This state can be quantitatively identified as the COD greater than 0. At this point, the oxygen balance is compromised and the anaerobic metabolism is initiated.

Patient state S4 refers to compensatory shock. This state may, for example, be quantitatively identified as COD between 50 to 120 mL/kg. When in compensatory shock, the physiology of the patient tries to compensate for the compromised oxygen balance by controlling different physiologic variables, such as increasing heart rate to assure sufficient cardiac output, peripheral vasorestriction to assure perfusion of vital organs, increased respiratory rate to counter the ensuing acidosis by faster removal of $CO_2$, etc.

Patient state S5 refers to progressive shock. This state may, for example, be quantitatively identified as COD greater than 120 mL/kg. At this point, the compensatory mechanisms of the physiology start failing, which leads to consequent failure of vital organs.

Patient state S6 refers to cardiac arrest, which similarly to the previous example is the major adverse effect of the compromised oxygen balance.

Still referring to FIG. 7, the probabilities $P_E$, $P_F$, $P_G$ and $P_H$ signify, respectively, the probabilities for the patient developing a cardiac arrest in a particular time interval, given hemorrhaging, initial shock, compensatory shock and progressive shock. The patient state probability module 138 can calculate these probabilities. It should be appreciated that $P_H>P_G>P_F>P_E$, i.e. the probability for cardiac arrest grows as the oxygen deficit increases. On the other hand, $P_A$, $P_B$, $P_C$, and $P_D$ signify the probabilities of return to spontaneous circulation after cardiac arrest. Again it should be appreciated that $P_A>P_B>P_C>P_D$, i.e. that the higher the oxygen deficit, the lower is the probability that the patient's heart rate returns to normal rhythm. Similar to FIG. 3, all arches shown in FIG. 7 can be endowed with probabilities ranging from, for example, 0 to 1 or 0% to 100%.

When the system 120 is initialized and no treatment has begun to be administered, the probabilities may be derived from static information, such as medical records, literature, physician inputs, and the like. However, as patient-specific information, such as physiological information and treatment information are provided, the probabilities may be updated based on the patient-specific information being fed to the system 120. As described above, the patient state probability determination module 138 may be configured to estimate the probabilities and update the probabilities as changes to the patient's physiology are observed. The probabilities may be dynamically updated by estimating how the patient is influenced by additional parameters, such as the resuscitative fluid infusion rate as described below:

The stated equations below employ the following notation:

- $x_1$ is the cumulative oxygen deficit, COD
- $x_2$ is the hemoglobin also denoted as Hgb
- $x_3$ is the heart's stroke volume
- $x_4$ is the total blood loss
- $vO_2$ is current oxygen consumption
- $NvO_2$ is a constant denoting nominal oxygen consumption
- HR is the current heart rate
- CO is cardiac output
- W is the patient weight
- $SaO_2$ is the arterial oxygen saturation
- $SvO_2$ is the mixed venous oxygen saturation
- $CaO_2$ is the arterial oxygen content
- $CvO_2$ is the mixed venous oxygen content
- U is the rate of fluid infusion which is a treatment variable
- NV is a constant denoting the nominal volume of blood (the volume of blood before the injury).
- $c_i$ are constants describing the model, which are specific for each state.
- $\mu_i$ White zero-mean Gaussian noises with different standard deviations.

Then, illustrative dynamic equations describing the evolution of the COD variable outside of the cardiac arrest state can be derived under the following assumptions and dependencies.

$$\dot{x}_1 = \frac{NvO_2 - vO_2}{W}, \tag{1}$$

where the oxygen consumption $vO_2$ can be derived from the Fick principle as:

$$vO_2 = CO \cdot (Ca0_2 - Cv0_2) = HR \cdot x3 \cdot 1.36 \cdot x_2 \cdot (SaO_2 - SvO_2).$$

In shock, the heart rate is a compensatory mechanism and can be assumed to be a function of the cumulative oxygen deficit. Therefore, $$HR = c_1 x_1 + \mu_1$$

Also, $SaO_2$ can be assumed to be constant equal to 0.99 (or 99% arterial oxygen saturation), and $SvO_2$ can be assumed to be a function of the oxygen deficit that can be written as:

$$SvO_2 = c_2 - c_3 \frac{NvO_2 - vO_2}{W}$$

When substituted back to equation (1) these assumptions and dependencies make $\dot{x}_1$, a function of the constants $c_i$ and the model variables $x_i$.

The next equation shows that the hemoglobin decreases as more fluid is infused to the patient:

$$\dot{x}_2 = -c_4 x_2 U + \mu_2. \tag{2}$$

Similarly the next equation shows that the stroke volume is decreased by the blood loss and increased by the infusion of fluids:

$$\dot{x}_4 = -c_5(x_4 - U) + \mu_3. \tag{3}$$

And the final equation shows that the rate of bleeding is a function of the fluid volume (the more the volume the faster is the bleeding rate):

$$\dot{x}_4 = -c_6(V - x_4 + U) + \mu_4. \tag{4}$$

where the constant co characterizes the injury.

By employing these equations, the system can estimate the infusion rate U that will maximize the probability of the patient being in the least possible harmful state at the estimated time of arrival at the admitting hospital, given the current values of the variables $x_1(0)$, $x_2(0)$, $x_3(0)$, $x_4(0)$.

Moreover, the system can simulate different scenarios of admitting centers and fluid infusion therapies. This will allow the system to identify the risks associate with each of the available triage and fluid therapy options, and identify the least risky pair of an admitting location and fluid therapy.

While the foregoing includes the best mode and, where appropriate, other modes of performing the disclosure, the disclosure should not be limited to specific apparatus configurations or method steps disclosed in this description of the preferred embodiment. Those skilled in the art will also recognize that the disclosure has a broad range of applications, and that the embodiments admit of a wide range of modifications without departing from the inventive concepts.

What is claimed is:

1. A system for event-driven patient monitoring and treatment of a patient comprising:

a computer processor;

a memory coupled to the processor, the memory having computer-executable instructions stored thereon, which when executed by the processor, cause the processor to:

receive patient-specific data associated with the patient, the patient-specific data comprising at least data from a blood oximeter coupled with the patient;

determine a plurality of physiological variables based on the received patient-specific data, the plurality of physiological variables including at least oxygen saturation;

define a state space partitioned into a plurality of possible clinical patient states defined by a plurality of boundaries, the plurality of possible patient states comprising:

(i) inadequate DO2 along with normal Qp/Qs;

(ii) adequate DO2 along with high Qp/Qs; and (iii) inadequate DO2 along with high Qp/Qs;

wherein a boundary between adequate DO2 and inadequate DO2 is 25 ml O2/min/kg;

determine from the patient-specific data, a current clinical patient state of the patient within the state space, the current clinical patient state being one of:

(a) inadequate DO2 along with normal Qp/Qs;

(b) adequate DO2 along with high Qp/Qs; and (c) inadequate DO2 along with high Qp/Qs; and send a signal to a treatment device coupled to the patient so that the signal causes the treatment device to administer a treatment to the patient, the treatment known to address the current clinical patient state.

2. The system of claim 1:

wherein a boundary between normal Qp/Qs and high Qp/Q is a ratio of 1.5, such that the patient state of adequate DO2 along with high Qp/Qs is defined by DO2 greater than 25 ml O2/min/kg along with Qp/Qs greater than a ratio of 1.5, and such that the patient state of inadequate DO2 along with high Qp/Qs is defined by DO2 less than 25 ml O2/min/kg along with Qp/Qs greater than a ratio of 1.5, and such that the patient state of inadequate DO2 along with normal Qp/Qs is defined by DO2 less than 25 ml O2/min/kg along with Qp/Qs less than a ratio of 1.5.

3. The system of claim 1, wherein (x) the treatment for inadequate DO2 along with normal Qp/Qs, and the treatment for inadequate DO2 along with high Qp/Qs, is administration of chronotropic medication; and (y) the treatment for adequate DO2 along with high Qp/Qs is administration of vasodilation medication.

4. A method for event driven patient monitoring and treatment of a patient comprising:

receiving, at a computer, patient-specific data associated with the patient, the patient-specific data comprising at least data from a blood oximeter coupled with the patient;

determining, by the computer, a plurality of physiological variables based on the received patient-specific data;

defining, by the computer, a state space partitioned into the plurality of possible clinical patient states defined by a plurality of boundaries, including a boundary between adequate DO2 and inadequate DO2, and a boundary between normal Qp/Qs and high Qp/Q, the plurality of possible patient states comprising:

(i) inadequate DO2 along with normal Qp/Qs;

(ii) adequate DO2 along with high Qp/Qs; and (iii) inadequate DO2 along with high Qp/Qs;

wherein a boundary between adequate DO2 and inadequate DO2 is 25 ml O2/min/kg;

determining, by the computer, from the physiological variables, a current clinical patient state within the state space, the current clinical patient state being one of:

inadequate DO2 along with normal Qp/Qs;

adequate DO2 along with high Qp/Qs; and inadequate DO2 along with high Qp/Qs; and sending a signal from the computer to a treatment device coupled to the patient so that the signal causes the treatment device to administer a treatment to the patient, the treatment known to address the current clinical patient state.

5. The method of claim 4:

wherein a boundary between normal Qp/Qs and high Qp/Q is a ratio of 1.5, such that the patient state of adequate DO2 along with high Qp/Qs is defined by DO2 greater than 25 ml O2/min/kg along with Qp/Qs greater than a ratio of 1.5, and such that the patient state of inadequate DO2 along with high Qp/Qs is defined by DO2 less than 25 ml O2/min/kg along with Qp/Qs greater than a ratio of 1.5, and such that the patient state of inadequate DO2 along with normal Qp/Qs is defined by DO2 less than 25 ml O2/min/kg along with Qp/Qs less than a ratio of 1.5.

6. The method of claim 4, wherein (x) the treatment for inadequate DO2 along with normal Qp/Qs, and the treatment for inadequate DO2 along with high Qp/Qs, is administration of chronotropic medication; and (y) the treatment for adequate DO2 along with high Qp/Qs is administration of vasodilation medication.

7. A non-transitory computer-readable medium having computer-executable instructions stored thereon, the instructions executable by a computer, the instructions comprising:

instructions to cause the computer to receive patient-specific data associated with the patient, the patient-specific data comprising at least data from one of a plurality of sensors coupled with the patient, the plurality of sensors including at least a blood oximeter;

instructions to cause the computer to determine a plurality of physiological variables based on the received patient-specific data, the plurality of physiological variables including at least oxygen saturation;

instructions to cause the computer to define a state space partitioned into a plurality of possible clinical patient states defined by a plurality of boundaries, the plurality of possible patient states comprising:

(i) inadequate DO2 along with normal Qp/Qs;

(ii) adequate DO2 along with high Qp/Qs; and (iii) inadequate DO2 along with high Qp/Qs;

wherein a boundary between adequate DO2 and inadequate DO2 is 25 ml O2/min/kg;

instructions to cause the computer to determine from the physiological variables, a current clinical patient state of the patient within the state space, the current clinical patient state being one of:

(a) inadequate DO2 along with normal Qp/Qs;

(b) adequate DO2 along with high Qp/Qs; and (c) inadequate DO2 along with high Qp/Qs; and instructions to cause the computer to control a treatment device by sending a signal to the treatment device coupled to the patient so that the signal causes the treatment device to administer a treatment to the patient, the treatment known to address the current clinical patient state.

8. The non-transitory computer-readable medium of claim 7:

wherein a boundary between normal Qp/Qs and high Qp/Q is a ratio of 1.5, such that the patient state of adequate DO2 along with high Qp/Qs is defined by DO2 greater than 25 ml O2/min/kg along with Qp/Qs greater than a ratio of 1.5, and such that the patient state of inadequate DO2 along with high Qp/Qs is defined by DO2 less than 25 ml O2/min/kg along with Qp/Qs greater than a ratio of 1.5, and such that the patient state of inadequate DO2 along with normal Qp/Qs is defined by DO2 less than 25 ml O2/min/kg along with Qp/Qs less than a ratio of 1.5.

9. The non-transitory computer-readable medium of claim 7, wherein (x) the treatment for inadequate DO2 along with normal Qp/Qs, and the treatment for inadequate DO2 along with high Qp/Qs is administration of chronotropic medication; and (y) the treatment for adequate DO2 along with high Qp/Qs is administration of vasodilation medication.

* * * * *